(12) United States Patent
Kovi et al.

(10) Patent No.: US 10,442,813 B2
(45) Date of Patent: Oct. 15, 2019

(54) POLYMORPHS OF RUCAPARIB CAMSYLATE AND METHODS OF MAKING SAME

(71) Applicant: RK Pharma Solutions LLC, Piscataway, NJ (US)

(72) Inventors: Ravishanker Kovi, Monroe, NJ (US); Jayaraman Kannapan, Gujarat (IN); Ananda Babu Thirunavakarasu, Gujarat (IN); Hemant Mande, Gujarat (IN)

(73) Assignee: RK PHARMA SOLUTIONS LLC, Piscataway, NJ (US)

( * ) Notice: Subject to any disclaimer, the term of this patent is extended or adjusted under 35 U.S.C. 154(b) by 0 days.

(21) Appl. No.: 16/260,978

(22) Filed: Jan. 29, 2019

(65) Prior Publication Data

US 2019/0233428 A1 Aug. 1, 2019

(30) Foreign Application Priority Data

Jan. 30, 2018 (IN) .............................. 201821003485
Apr. 10, 2018 (IN) .............................. 201821013649
Jan. 29, 2019 (IN) .............................. 201821003485

(51) Int. Cl.
*C07D 487/06* (2006.01)

(52) U.S. Cl.
CPC ........ *C07D 487/06* (2013.01); *C07B 2200/13* (2013.01)

(58) Field of Classification Search
CPC .................................................... C07D 487/06
See application file for complete search history.

(56) References Cited

U.S. PATENT DOCUMENTS

| | | | |
|---|---|---|---|
| 6,495,541 B1 | 12/2002 | Webber | |
| 7,268,126 B2 | 9/2007 | Liu | |
| 8,754,072 B2 | 6/2014 | Basford | |

*Primary Examiner* — Bruck Kifle
(74) *Attorney, Agent, or Firm* — Timothy X. Gibson, Esq.; Gibson & Dernier LLP

(57) ABSTRACT

Novel polymorphs of rucaparib camsylate include Form alpha having XRPD peaks at diffraction angles (2θ) of 6.14±0.2, 12.41±0.2, 15.34±0.2, 15.95±0.2, 16.36±0.2, 16.51±0.2 and 19.67±0.2, Form beta having XRPD peaks at diffraction angles (2θ) of 6.86±0.2, 9.58±0.2, 12.75±0.2, 14.56±0.2, 15.05±0.2, 20.76±0.2 and 22.45±0.2, and Form gamma having XRPD peaks at diffraction angles (2θ) of 9.5±0.2, 12.73±0.2, 14.77±0.2, 15.16±0.2, 20.62±0.2, 22.33±0.2, 22.63±0.2 and 27.29±0.2. Methods are disclosed for the preparation of such polymorphic forms and pharmaceutical compositions containing such polymorphic forms. A method is disclosed for preparing a highly pure Form B of rucaparib camsylate. Pharmaceutical compositions containing highly pure Form B prepared by the method are disclosed.

16 Claims, 10 Drawing Sheets

POLYMORPHS OF RUCAPARIB CAMSYLATE AND METHODS OF MAKING SAME

CROSS-REFERENCE TO RELATED APPLICATIONS

This application claims the benefit of the earlier fling date of Indian Provisional Patent Application Nos. IN201821003485 filed 30 Jan. 2018, IN201821013649 filed 10 Apr. 2018, and Indian Nonprovisional Patent Application No. IN201821003485 filed Jan. 29, 2019, each of which are hereby incorporated by reference in their entireties.

FIELD OF THE INVENTION

The present invention relates to rucaparib camsylate. Specifically, the present invention relates to novel crystalline forms of rucaparib camsylate, methods for the preparation of such polymorphic forms and pharmaceutical compositions containing such polymorphic forms.

BACKGROUND

Rucaparib camsylate ($C_{19}H_{18}FN_3O \cdot C_{10}H_{10}O_4S$, chemical name 8-fluoro-2-{4-[(methylamino) methyl] phenyl}-1,3,4,5-tetrahydro-6H-azepino[5,4,3-cd]indol-6-one ((1S,4R)-7,7dimethyl-2-oxobicyclo[2.2.1]hept-1-yl) methanesulfonic acid salt, relative molecular mass 555.67 Daltons) is an inhibitor of the mammalian polyadenosine 5'-diphosphoribose polymerase (PARP) enzyme used as an anti-cancer agent and has the following chemical structure:

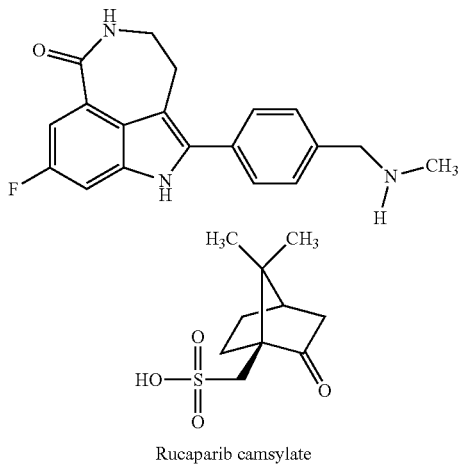

Rucaparib camsylate

Rucaparib camsylate is marketed by Pfizer under the trade name Rubraca®. Rubraca® tablets are intended for oral administration only and are available in various dosages. For example, each Rubraca® 200 mg tablet contains 344 mg rucaparib camsylate equivalent to 200 mg rucaparib free base. The tablets also contain the inactive ingredients microcrystalline cellulose, sodium starch glycolate, colloidal silicon dioxide, and magnesium stearate.

SUMMARY OF THE INVENTION

The present application provides various novel crystalline forms of rucaparib camsylate and methods of preparation thereof.

In one or more embodiments, the present application provides crystalline Form alpha of rucaparib camsylate having an XRPD pattern having peaks at diffraction angles (2θ) of 6.14±0.2, 12.41±0.2, 15.34±0.2, 15.95±0.2, 16.36±0.2, 16.51±0.2 and 19.67±0.2.

In other embodiments, the present application provides crystalline Form alpha of rucaparib camsylate having an XRPD pattern having peaks at diffraction angles (2θ) of 6.14±0.2, 12.41±0.2, 15.34±0.2, 15.95±0.2, 16.36±0.2, 16.51±0.2, 18.54±0.2, 19.67±0.2, 22.68±0.2 and 23.21±0.2.

In still further embodiments, the present application provides crystalline Form alpha of rucaparib camsylate having an XRPD pattern having peaks at diffraction angles (2θ) of 6.14±0.2, 12.41±0.2, 14.48±0.2, 15.34±0.2, 15.95±0.2, 16.36±0.2, 16.51±0.2, 17.15±0.2, 18.22±0.2, 18.54±0.2, 19.67±0.2, 22.68±0.2, 23.21±0.2, and 24.90±0.2.

In yet further embodiments, the present application provides crystalline Form alpha of rucaparib camsylate having an x-ray powder diffraction (XRPD) pattern as illustrated by FIG. 1.

In still further embodiments, the present application provides crystalline Form alpha of rucaparib camsylate having a differential scanning calorimetry (DSC) pattern as illustrated by FIG. 2.

In another embodiment, the present application provides processes for preparing crystalline Form alpha rucaparib S-camsylate, including the steps of:
a) reacting rucaparib free base with S-camphorsulfonic acid in a suitable solvent;
b) isolating crystalline Form alpha rucaparib S-camsylate.

In another embodiment, the present application provides a pharmaceutical composition including a crystalline Form alpha of rucaparib camsylate and one or more pharmaceutically acceptable excipients.

In one or more embodiments, the present application provides crystalline Form beta of rucaparib camsylate having an XRPD pattern having peaks at diffraction angles (2θ) of 6.86±0.2, 9.58±0.2, 12.75±0.2, 14.56±0.2, 15.05±0.2, 20.76±0.2 and 22.45±0.2.

In one or more embodiments, the present application provides crystalline Form beta of rucaparib camsylate having an XRPD pattern having peaks at diffraction angles (2θ) of 6.86±0.2, 9.58±0.2, 12.75±0.2, 14.56±0.2, 15.05±0.2, 15.41±0.2, 15.99±0.2, 20.76±0.2, 22.45±0.2 and 27.44±0.2.

In one or more embodiments, the present application provides crystalline Form beta of rucaparib camsylate having an XRPD pattern having peaks at diffraction angles (2θ) of 6.86±0.2, 9.58±0.2, 11.08±0.2, 12.75±0.2, 14.56±0.2, 15.05±0.2, 15.41±0.2, 15.99±0.2, 19.35±0.2, 19.59±0.2, 20.76±0.2, 22.11±0.2, 22.45±0.2, 23.80±0.2, and 27.44±0.2.

In yet further embodiments, the present application provides crystalline Form beta of rucaparib camsylate having an XRPD pattern as illustrated by FIG. 3. In still further embodiments, the present application provides crystalline Form beta of rucaparib camsylate having a DSC pattern as illustrated by FIG. 4.

In another embodiment, the present application provides processes for preparing novel crystalline Form beta of rucaparib camsylate including the steps of:
a) reacting rucaparib free base with DL-10-camphorsulfonic acid in a suitable solvent;
b) isolating crystalline Form beta of rucaparib camsylate.

In another embodiment, the present application provides a pharmaceutical composition including a highly pure novel crystalline Form beta of rucaparib camsylate salt and one or more pharmaceutically acceptable excipients.

In another embodiment, the present application provides crystalline highly pure rucaparib camsylate Form B that is substantially free of other polymorphic and chemical contaminations that can be characterized by its XRPD pattern as illustrated by FIG. 5.

In still further embodiments the present application provides a highly pure crystalline Form B of rucaparib camsylate having a DSC pattern as illustrated by FIG. 6.

In another embodiment, the present application provides processes for preparing a highly pure Form B of rucaparib camsylate, including the steps of:

a) reacting rucaparib free base with DL-10-camphorsulfonic acid or racemic camphorsulfonic acid in a suitable solvent; and b) isolating highly pure crystalline rucaparib camsylate Form B.

Any physical form of rucaparib free base may be utilized in step (a) of the process. In one embodiment, the form of rucaparib is rucaparib free base. In one embodiment, the camsylate salt used in step (a) is DL-10-camphorsulfonic acid.

In another embodiment, the present application provides a pharmaceutical composition including a highly pure crystalline Form B of rucaparib camsylate salt and one or more pharmaceutically acceptable excipients.

In still further embodiments, the present application provides crystalline Form gamma of rucaparib camsylate having an XRPD pattern having peaks at diffraction angles (2θ) 9.5±0.2, 12.73±0.2, 14.77±0.2, 15.16±0.2, 20.62±0.2, 22.33±0.2, 22.63±0.2 and 27.29±0.2.

In still further embodiments, the present application provides crystalline Form gamma of rucaparib camsylate having an XRPD pattern having peaks at diffraction angles (2θ) 9.5±0.2, 12.73±0.2, 14.77±0.2, 15.16±0.2, 20.62±0.2, 20.95±0.2, 22.11±0.2, 22.33±0.2, 22.63±0.2, 23.57±0.2 and 27.29±0.2.

In still yet further embodiments, the present application provides crystalline Form gamma of rucaparib camsylate having an XRPD pattern having peaks at diffraction angles (2θ) 6.95±0.2, 9.5±0.2, 12.73±0.2, 14.77±0.2, 15.16±0.2, 20.62±0.2, 20.95±0.2, 21.45±0.2, 22.11±0.2, 22.33±0.2, 22.63±0.2, 23.57±0.2, 23.93±0.2, 26.71±0.2, and 27.29±0.2.

In yet further embodiments, the present application provides crystalline Form gamma of rucaparib camsylate having an XRPD pattern as illustrated by FIG. 8. In still further embodiments, the present application provides crystalline Form gamma of rucaparib camsylate having a DSC pattern as illustrated by FIG. 9. In still further embodiments, the present application provides crystalline Form gamma of rucaparib camsylate having a characteristic thermogravimetric analysis (TGA) as illustrated by FIG. 10.

In another embodiment, the present application provides processes for preparing crystalline Form gamma rucaparib camsylate, including the steps of:

a) combining rucaparib free base with a suitable solvent such as methanol to achieve a clear solution, b) reacting the resulting clear solution with S-camphorsulfonic acid; and c) isolating crystalline Form gamma rucaparib camsylate.

In another embodiment, the present application provides a pharmaceutical composition including a crystalline Form gamma of rucaparib camsylate and one or more pharmaceutically acceptable excipients.

BRIEF DESCRIPTION OF THE DRAWINGS

For the purposes of illustration, there are forms shown in the drawings that are presently preferred, it being understood, however, that the invention is not limited to the precise embodiments shown.

DETAILED DESCRIPTION OF THE INVENTION

Figure 1:
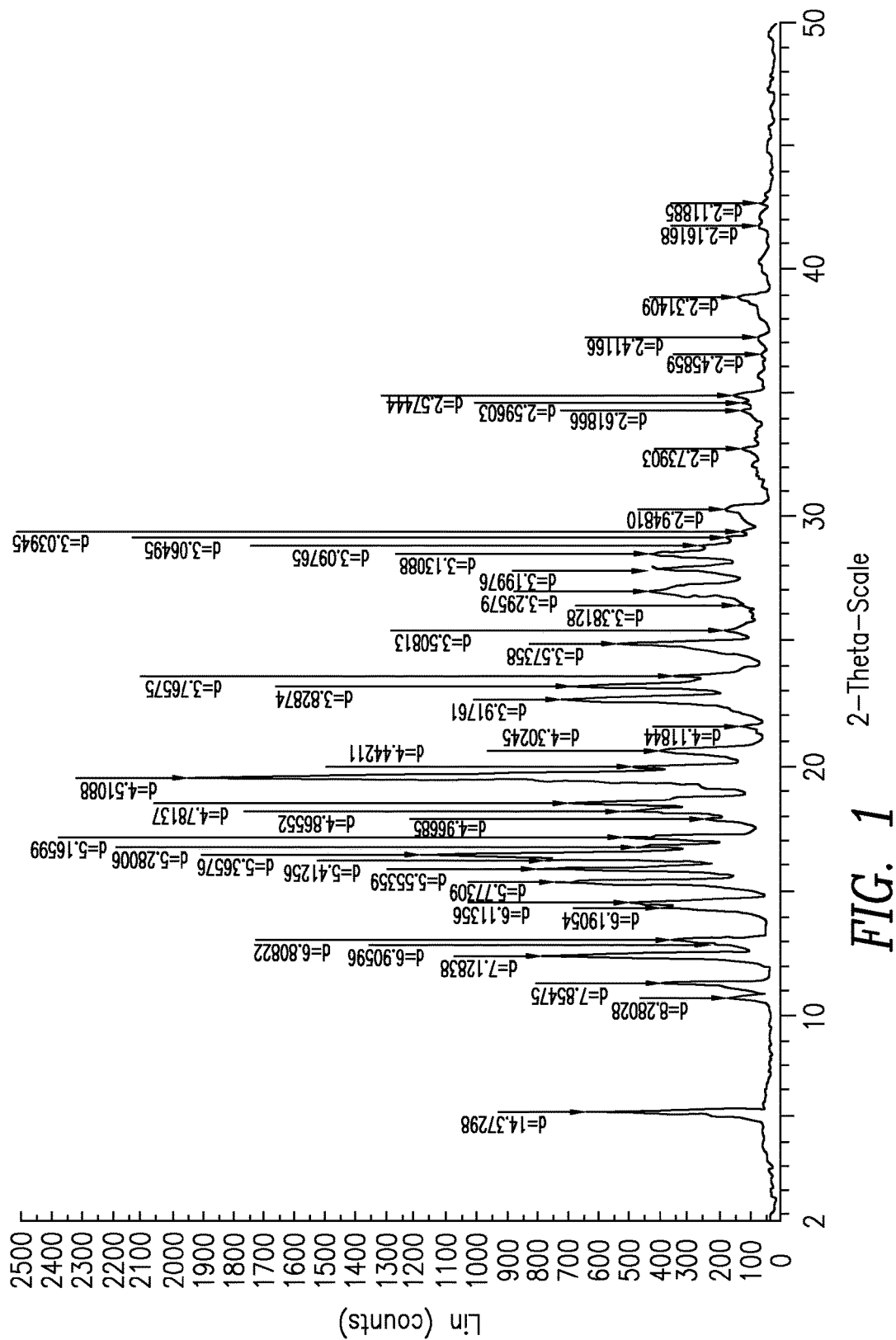
FIG. 1 is a graphical depiction of a characteristic XRPD of rucaparib camsylate Form alpha obtained using copper K-alpha$_1$ X-rays at a wavelength of 1.5406 Ångstroms according to an embodiment of the present disclosure.

Embodiments of the present invention now will be described more fully hereinafter with reference to the accompanying examples and experiments, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All percentages and ratios used herein are by weight of the total composition and all measurements made are at 25° C. and normal pressure unless otherwise designated. All temperatures are in degrees Celsius unless specified otherwise. In some embodiments.

As used herein, "comprising" means the elements recited, or their equivalent in structure or function, plus any other element or elements which are not recited.

All ranges recited herein include the endpoints, including those that recite a range "between" two values.

The difference in the physical properties of different crystalline form results from the orientation and intermolecular interaction of adjacent molecules or complexes in the bulk solid. Accordingly polymorphs are distinct solids sharing the same molecular formula yet having advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubility.

U.S. Pat. No. 6,495,541 discloses the compound rucaparib. U.S. Pat. No. 7,268,126 appears to claim rucaparib phosphate salts of various crystalline polymorphic forms such as Form I, II, III, V, VI. U.S. Pat. No. 8,754,072 appears to claim crystalline camsylate and maleate salts of rucaparib, including Form A, Form B, and Form C and amorphous form of rucaparib camsylate and Form A of Rucaparib maleate. U.S. Pat. No. 8,754,072 also appears to claim a crystalline camsylate salt of rucaparib wherein the salt has a powder X-ray diffraction pattern comprising one or more or two or more or three peaks at diffraction angles (2θ) selected from the group consisting of 12.2±0.2, 14.8±0.2 and 22.4±0.2, wherein said powder X-ray diffraction pattern is obtained using copper K-alpha$_1$ X-rays at a wavelength of 1.5406 Ångstroms.

Polymorphism, the occurrence of different crystal form is a property of some molecules and molecular complexes. A single molecule may have a variety of crystalline forms having distinct crystal structures and physical properties like melting point, X-ray diffraction pattern, infra absorption fingerprint, and solid state NMR spectrum. One crystalline form may give rise to thermal behaviour different from that of another crystalline form.

The discovery of new polymorphic forms or solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristics. Therefore, there is a need for additional crystalline forms of rucaparib camsylate.

Since improved drug formulations are consistently sought, there is an ongoing need for new or purer polymorphic form of existing drug molecules. The present disclosure describes novel crystalline forms of Rucaparib camsylate and processes for the preparation thereof that help to meet aforementioned and other needs.

In one or more embodiments, crystalline Form alpha of rucaparib camsylate is disclosed having characteristic XRPD peaks at diffraction angles (2θ) of 6.14±0.2, 12.41±0.2, 15.34±0.2, 15.95±0.2, 16.36±0.2, 16.51±0.2 and 19.67±0.2.

In other embodiments, crystalline Form alpha of rucaparib is disclosed having characteristic XRPD peaks at diffraction angles (2θ) of 6.14±0.2, 12.41±0.2, 15.34±0.2, 15.95±0.2, 16.36±0.2, 16.51±0.2, 18.54±0.2, 19.67±0.2, 22.68±0.2 and 23.21±0.2.

In still further embodiments, crystalline Form alpha of rucaparib camsylate is disclosed having characteristic XRPD peaks at diffraction angles (2θ) of 6.14±0.2, 12.41±0.2, 14.48±0.2, 15.34±0.2, 15.95±0.2, 16.36±0.2, 16.51±0.2, 17.15±0.2, 18.22±0.2, 18.54±0.2, 19.67±0.2, 22.68±0.2, 23.21±0.2, and 24.90±0.2.

In yet further embodiments, crystalline Form alpha of rucaparib camsylate can be characterized by its XRPD pattern as illustrated by Table 1 and FIG. 1.

TABLE 1

Form alpha XRPD of FIG. 1

| Angle (Degree 2θ ± 0.2°) | d value (Angstroms) | Intensity % |
|---|---|---|
| 6.1443 | 14.37298 | 32.6 |
| 10.6757 | 8.28028 | 8.3 |
| 11.2559 | 7.85475 | 19.6 |
| 12.4071 | 7.12838 | 40.0 |
| 12.8083 | 6.90596 | 10.8 |
| 12.9930 | 6.80822 | 18.2 |
| 14.2959 | 6.19054 | 19.6 |
| 14.4769 | 6.11356 | 24.9 |
| 15.3356 | 5.77309 | 37.7 |
| 15.9456 | 5.55359 | 40.6 |
| 16.3639 | 5.41256 | 39.5 |
| 16.5076 | 5.36576 | 60.2 |
| 16.7775 | 5.28006 | 23.4 |
| 17.1507 | 5.16599 | 26.2 |
| 17.8438 | 4.96685 | 11.7 |
| 18.2186 | 4.86552 | 26.3 |
| 18.5420 | 4.78137 | 35.3 |
| 19.6646 | 4.51088 | 100.0 |
| 19.9721 | 4.44211 | 24.0 |
| 20.6274 | 4.30245 | 19.7 |
| 21.5598 | 4.11844 | 5.8 |
| 22.6794 | 3.91761 | 36.7 |
| 23.2130 | 3.82874 | 33.6 |
| 23.6068 | 3.76575 | 16.4 |
| 24.8961 | 3.57358 | 26.5 |
| 25.3683 | 3.50813 | 8.2 |
| 26.3367 | 3.38128 | 6.1 |
| 27.0326 | 3.29579 | 21.0 |
| 27.8601 | 3.19976 | 19.9 |
| 28.4858 | 3.13088 | 21.6 |
| 28.7979 | 3.09765 | 12.6 |
| 29.1119 | 3.06495 | 8.6 |
| 29.3617 | 3.03945 | 5.9 |
| 30.2929 | 2.94810 | 8.6 |
| 32.6674 | 2.73903 | 5.7 |
| 34.2141 | 2.61866 | 5.8 |
| 34.5217 | 2.59603 | 5.6 |
| 34.8204 | 2.57444 | 7.3 |
| 36.5176 | 2.45859 | 3.2 |
| 37.2540 | 2.41166 | 3.4 |
| 38.8866 | 2.31409 | 6.7 |
| 41.7515 | 2.16168 | 3.4 |
| 42.6363 | 2.11885 | 3.0 |

Figure 2:
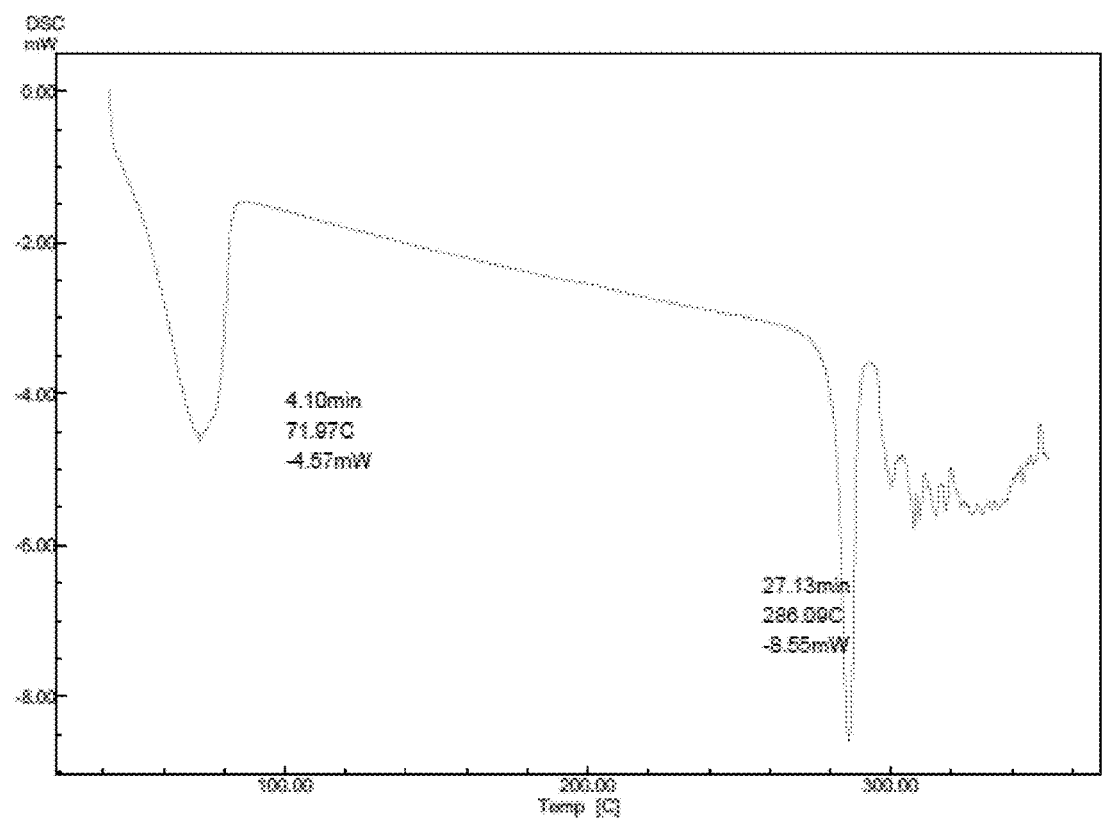
FIG. 2 is a graphical depiction of a characteristic DSC pattern of rucaparib camsylate Form alpha according to an embodiment of the present disclosure.

In at least one embodiment crystalline Form alpha of rucaparib camsylate may have a differential scanning calorimetry (DSC) pattern substantially as shown FIG. 2.

Rucaparib camsylate Form alpha may be made using a process which includes the steps of a) reacting rucaparib free base with S-camphorsulfonic acid in a suitable solvent; and b) isolating crystalline pure Form alpha rucaparib camsylate salt.

Suitable solvents which can be used in step (a) for the preparation of Form alpha rucaparib camsylate include cyclic ether such as tetrahydrofuran, furan, ethylene oxide, and the like; water; and any mixtures of two or more thereof.

The solution obtained in step (a) may be filtered to remove any insoluble particles. Suitable techniques to remove insoluble particles are filtration, micron filter, centrifugation, decantation, and any other techniques known in the art. The solution can be filtered by passing through paper, or other membrane material, or a clarifying agent such as celite. Depending upon the equipment used and the concentration and temperature of the solution, the filtration apparatus may need to be preheated to avoid premature precipitation of solid.

Step (b) involves isolating Form alpha rucaparib camsylate. The isolation of crystalline Form alpha of rucaparib camsylate may be induced by using conventional techniques known in the art. For example, useful techniques include but are not limited to, concentrating, cooling, stirring, shaking, combining with an anti-solvent, adding seed crystals, evaporation, flash evaporation, simple evaporation, rotational drying, or the like. The solid that is obtained may carry a small proportion of occluded mother liquor containing a higher percentage of impurities and, if desired, the solid may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, fluidized bed drying. The recovery of crystalline Form alpha can be done by decantation, centrifugation, gravity filtration, suction filtration and like. The solvent can be removed, optionally under reduced pressures, at temperatures less than about 60° C., less than about 50° C., less than about 40° C. or any other suitable temperatures.

In another aspect present application involves recovery of crystalline rucaparib camsylate salt after removal of solvent. The recovery can be done by using processes known in the art. The resulting solid may be collected by using techniques such as by scraping, or by shaking the container, or other techniques specific to the equipment used. The isolated solid may be optionally further dried to afford crystalline Rucaparib camsylate salt.

The resulting compound may be optionally further dried. Drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about 60° C., less than about 40° C., less than about 30° C., less than about 20° C., or any other suitable temperatures; at atmospheric pressure or under a reduced pressure; as long as the crystalline Rucaparib camsylate salt is not degraded in its quality. The drying can be carried out for any desired times until the required product quality is achieved. Suitable time for drying can vary from few minutes to several hours for example from about 30 minutes to about 24 or more hours.

It is believed that rucaparib S-camsylate salt Form alpha is a solvate. It is further believed that rucaparib camsylate Form alpha is a 1, 4-dioxane solvate which has a ratio of rucaparib camsylate to 1, 4-dioxane of 1:1.

Once obtained, crystals of rucaparib camsylate salt Form alpha may be used as the nucleating agent or "seed" crystals for subsequent crystallizations of Rucaparib camsylate salt Form alpha from a solution.

In still further embodiments, crystalline Form beta of rucaparib camsylate is disclosed having characteristic XRPD peaks at diffraction angles (2θ) of 6.86±0.2, 9.58±0.2, 12.75±0.2, 14.56±0.2, 15.05±0.2, 20.76±0.2 and 22.45±0.2.

In one or more embodiments, crystalline Form beta of rucaparib camsylate is disclosed having characteristic XRPD peaks at diffraction angles (2θ) of 6.86±0.2, 9.58±0.2, 12.75±0.2, 14.56±0.2, 15.05±0.2, 15.41±0.2, 15.99±0.2, 20.76±0.2, 22.45±0.2 and 27.44±0.2.

In still further embodiments, crystalline Form beta of rucaparib camsylate is disclosed having characteristic XRPD peaks at diffraction angles (2θ) of 6.86±0.2, 9.58±0.2, 11.08±0.2, 12.75±0.2, 14.56±0.2, 15.05±0.2, 15.41±0.2, 15.99±0.2, 19.35±0.2, 19.59±0.2, 20.76±0.2, 22.11±0.2, 22.45±0.2, 23.80±0.2, and 27.44±0.2.

Figure 3:
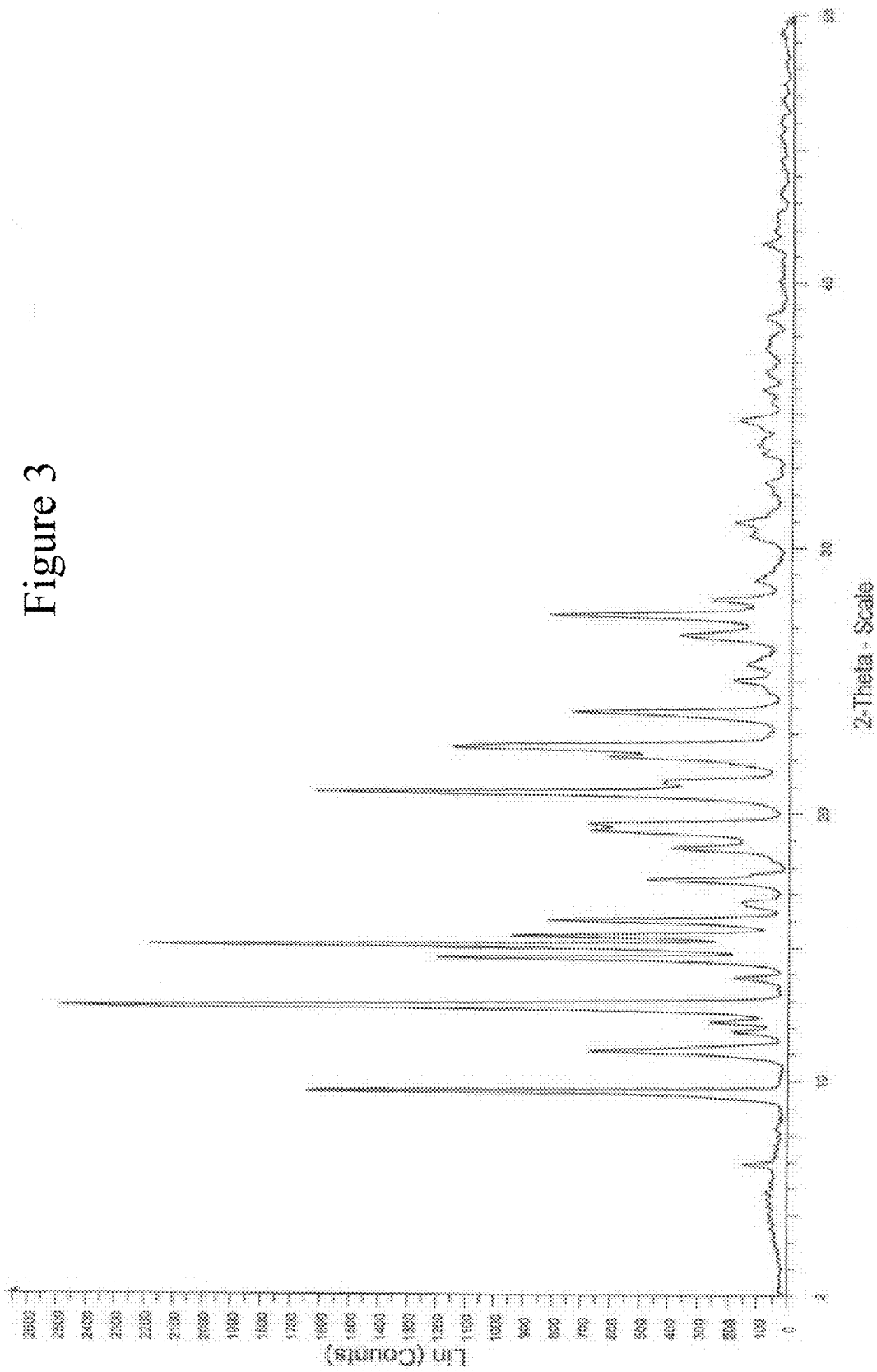
FIG. 3 is a graphical depiction of a characteristic XRPD pattern of rucaparib camsylate Form beta obtained using copper K-alpha$_1$ X-rays at a wavelength of 1.5406 Ångstroms according to an embodiment of the present disclosure.

In yet further embodiments, crystalline Form beta of rucaparib camsylate can be characterized by its XRPD pattern as illustrated by Table 2 and FIG. 3.

TABLE 2

Form beta XRPD of FIG. 3

| Angle (Degree 2θ ± 0.2°) | d value (Angstroms) | Intensity % |
|---|---|---|
| 6.8625 | 12.87025 | 5.8 |
| 9.5776 | 9.22702 | 66.0 |
| 11.0779 | 7.98051 | 26.9 |
| 11.7987 | 7.49453 | 7.3 |
| 12.1707 | 7.26633 | 10.3 |
| 12.7466 | 6.93927 | 100.0 |
| 13.8349 | 6.39576 | 7.2 |
| 14.5853 | 6.06836 | 48.0 |
| 15.0539 | 5.88050 | 87.8 |
| 15.4057 | 5.74697 | 37.8 |
| 15.9914 | 5.53779 | 32.9 |
| 16.6707 | 5.31365 | 6.3 |
| 17.4998 | 5.06372 | 19.1 |
| 18.6937 | 4.74290 | 15.7 |
| 19.3498 | 4.58356 | 26.9 |
| 19.5863 | 4.52872 | 27.2 |
| 20.7624 | 4.27478 | 65.0 |
| 21.2080 | 4.18595 | 16.7 |
| 22.1071 | 4.01771 | 24.4 |
| 22.4534 | 3.95651 | 46.2 |
| 23.7982 | 3.73589 | 29.5 |
| 25.0008 | 3.55885 | 7.4 |
| 25.5721 | 3.48061 | 5.7 |
| 26.6724 | 3.33948 | 14.7 |
| 27.4339 | 3.24849 | 32.7 |
| 28.0204 | 3.18181 | 10.2 |
| 28.7387 | 3.10390 | 4.6 |
| 30.4369 | 2.93448 | 5.5 |
| 30.9483 | 2.88714 | 7.5 |
| 32.4459 | 2.75722 | 3.4 |
| 33.5380 | 2.66989 | 3.9 |
| 34.7872 | 2.57682 | 6.9 |
| 35.4802 | 2.52807 | 2.8 |
| 35.9473 | 2.49628 | 3.9 |
| 36.6628 | 2.44918 | 3.6 |
| 38.6608 | 2.32708 | 3.6 |
| 41.4904 | 2.17468 | 4.0 |

Figure 4:
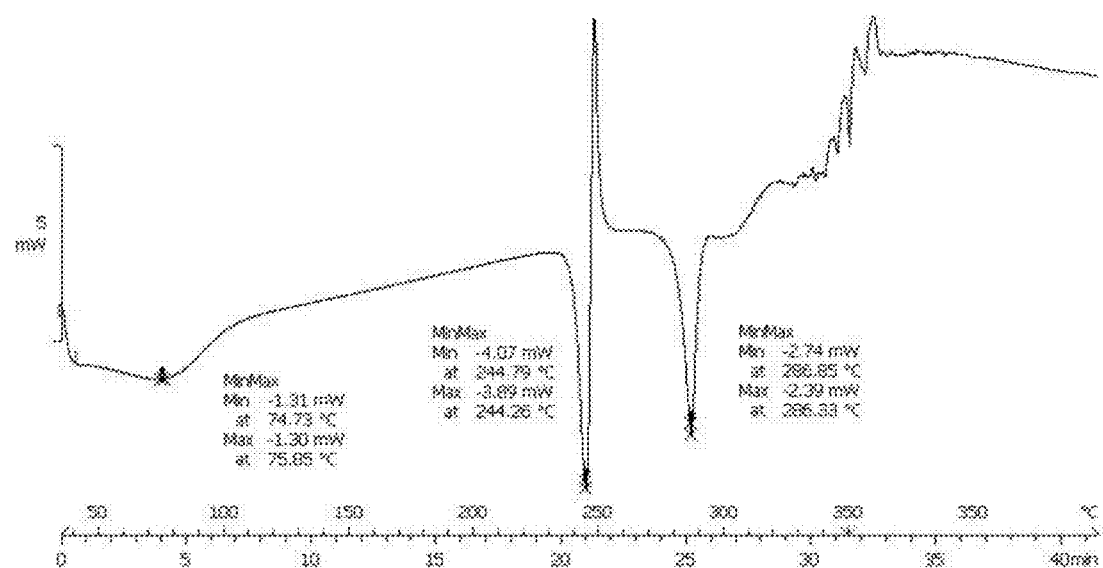
FIG. 4 is a graphical depiction of a characteristic DSC pattern of rucaparib camsylate Form beta according to an embodiment of the present disclosure.

In still further embodiments crystalline Form beta of rucaparib camsylate has an endothermic differential scanning calorimetric (DSC) thermogram. In some embodiments, crystalline Form beta has a DSC thermogram including an endothermic event with peak temperature at about 244° C. and another endothermic peak at 286° C. In at least one embodiment crystalline Form beta has a DSC thermogram substantially as shown in FIG. 4.

In one embodiment, a process for preparing rucaparib camsylate Form beta, includes the steps of:

a) reacting rucaparib free base with DL-10-camphorsulfonic acid in a suitable solvent; and b) isolating crystalline pure Form beta rucaparib camsylate salt.

Suitable solvents which can be used in step (a) for the preparation of rucaparib camsylate Form beta include nitriles such as acetonitrile, propionitrile and the like; acyclic ether such as ethyl methyl ether, 1,2-dimethoxyethane and the like, alcoholic solvents like methanol, ethanol, isopropanol, butanol, 2-methoxy ethanol, benzyl alcohol and the like; solvents like DMSO, DMF, DMA, N-methyl morpholine, N-Methyl-2-pyrrolidone and the like, water and any mixtures of two or more thereof.

The solution obtained in step (a) may be filtered to remove any insoluble particles. Suitable techniques to remove insoluble particles are filtration, micron filter, centrifugation, decantation, and any other techniques known in the art. The solution can be filtered by passing through paper, or other membrane material, or a clarifying agent such as celite. Depending upon the equipment used and the concentration and temperature of the solution, the filtration apparatus may need to be preheated to avoid premature precipitation of solid.

Step (b) involves isolating Form beta rucaparib camsylate, which may be induced by using conventional techniques known in the art. For example, useful techniques include but are not limited to, concentrating, cooling, stirring, shaking, combining with an anti-solvent, adding seed crystals, evaporation, flash evaporation, simple evaporation, or the like. The solid that is obtained may carry a small proportion of occluded mother liquor containing a higher percentage of impurities and, if desired, the solid may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, fluidized bed drying. The recovery of crystalline Form beta can be done by decantation, centrifugation, gravity filtration, suction filtration and like.

The solvent can be removed, optionally under reduced pressures, at temperatures less than about 60° C., less than about 50° C., less than about 40° C. or any other suitable temperatures.

Recovery and optional drying of Form beta crystalline rucaparib camsylate salt after removal of solvent may be performed in the manner set forth above with respect to Form alpha.

Once obtained, crystals of rucaparib camsylate salt Form beta may be used as the nucleating agent or "seed" crystals for subsequent crystallizations of rucaparib camsylate salt Form beta from solution.

The solubility of rucaparib camsylate Form beta was investigated in USP standard buffers adjusted to different pHs. For pH 1.2, the buffer solution included 3.73 g of potassium chloride dissolved in 100 ml of water which was mixed with 25 ml of 0.2 M hydrochloric acid. Water was added to bring the volume to 1000 ml. For pH 4.5, the buffer solution included 2.99 g of sodium acetate dissolved in 100 ml of water which was mixed with 14 ml of 2 N acetic acid. Water was added to bring the volume to 1000 ml. For pH 6.0, the buffer preparation included 6.80 g of potassium phosphate dissolved in 100 ml of water which was mixed with 28 ml of 0.2 M sodium hydroxide. Water was added to bring the volume to 1000 ml. For pH 6.8, the buffer preparation included 6.80 g of potassium phosphate dissolved in 100 ml of water, which was mixed with 112 ml of 0.2 M sodium hydroxide. Water was added to volume of 1000 ml. For pH 8.0, the buffer preparation included 3.09 of boric acid and 3.73 g of potassium chloride dissolved in 100 ml of water, which was mixed with 19.5 ml of 0.2 sodium hydroxide. Water was added to bring volume to 1000 ml.

Table 3 below shows the results of the solubility test. As shown in Table 3, rucaparib camsylate Form beta is practically insoluble in most pH values, with the exception of pH 8, where it is slightly soluble.

TABLE 3

Solubility Profile of Rucaparib Form beta in USP buffers at 37° C.

| S. No. | (USP) Buffer pH | Solubility |
|---|---|---|
| 1 | pH 1.2 | Practically insoluble (<0.1 mg/mL) |
| 2 | pH 4.5 | Practically insoluble (<0.1 mg/mL) |
| 3 | pH 6.0 | Practically insoluble (<0.1 mg/mL) |
| 4 | pH 6.8 | Practically insoluble (<0.1 mg/mL) |
| 5 | pH 8.0 | Very slightly soluble |
| 6 | Water | Practically insoluble (<0.1 mg/mL) |

In another embodiment, disclosed herein are methods of producing highly pure crystalline rucaparib camsylate Form B which is free of other polymorphic contaminations. Using the processes disclosed herein, rucaparib camsylate Form B may be produced having the XRPD pattern as shown in FIG. 5 and Table 4 and a DSC as shown in FIG. 6.

TABLE 4

Figure 5:
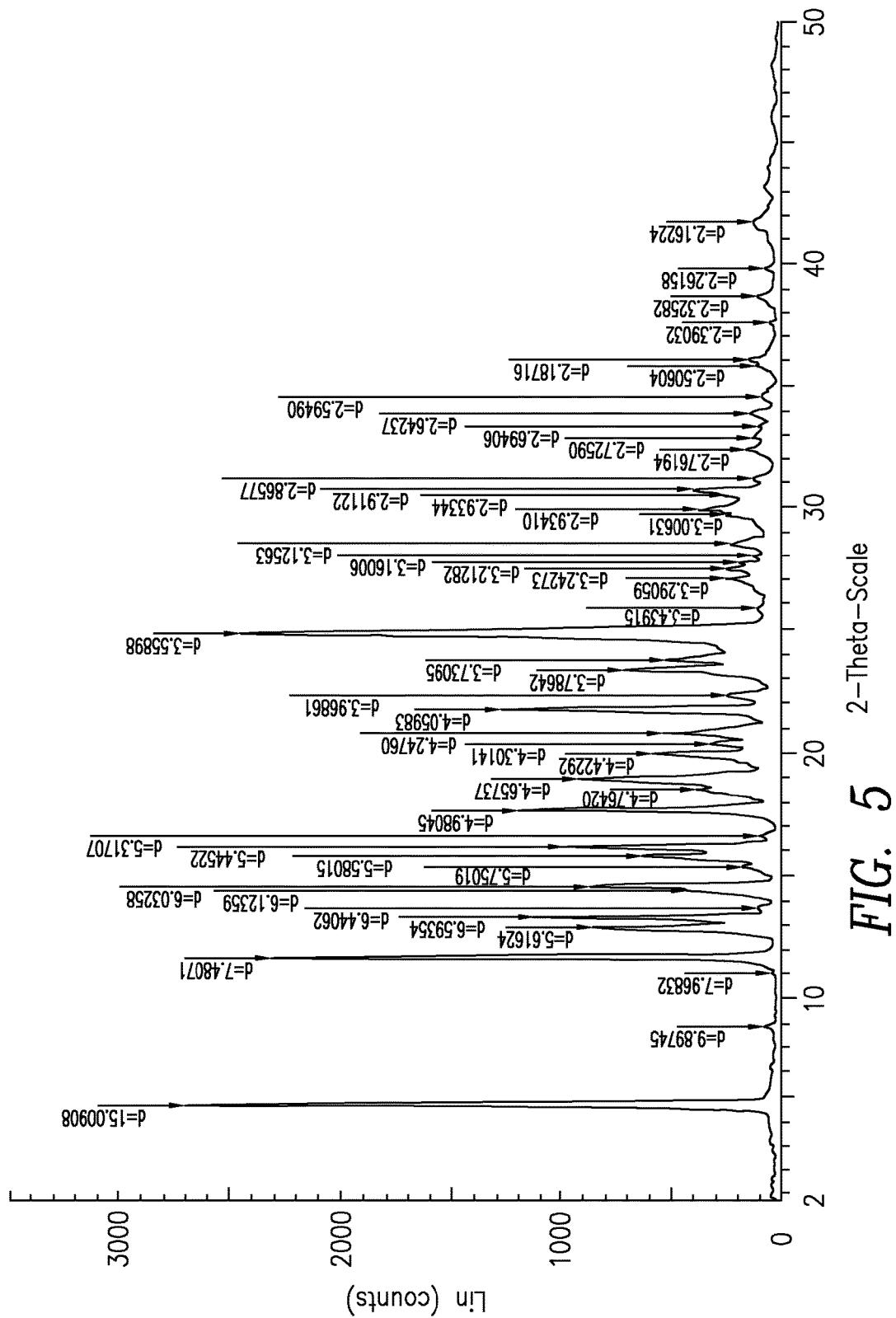
FIG. 5 is a graphical depiction of a characteristic XRPD pattern of rucaparib camsylate Form B obtained using copper K-alpha$_1$ X-rays at a wavelength of 1.5406 Ångstroms_according to an embodiment of the present disclosure.
Figure 6:
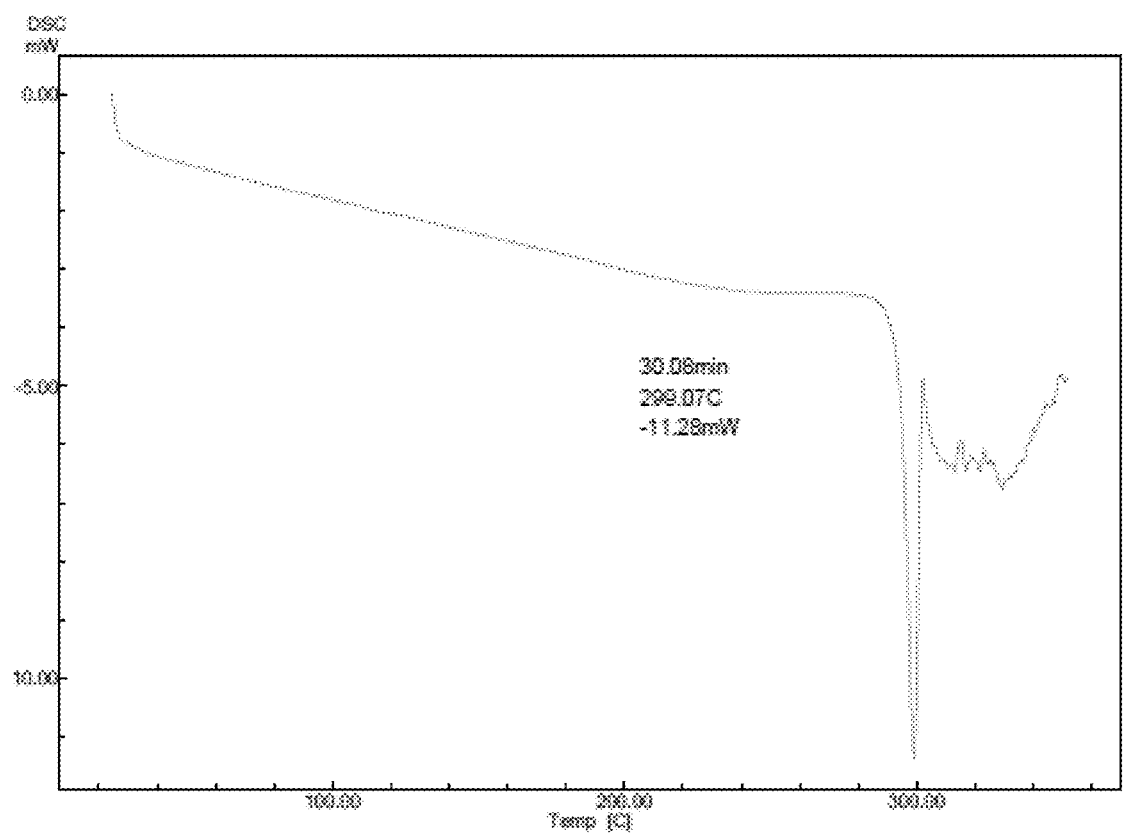
FIG. 6 is a graphical depiction of a characteristic DSC pattern of rucaparib camsylate Form B according to an embodiment of the present disclosure.

Form B XRPD of FIG. 5

| Angle (Degree 2θ ± 0.2°) | d value (Angstroms) | Intensity % |
|---|---|---|
| 5.88 | 15.00908 | 100 |
| 11.82 | 7.48071 | 85.3 |
| 12.97 | 6.81624 | 31.4 |
| 13.41 | 6.59354 | 41.7 |
| 14.67 | 6.03258 | 32 |
| 15.86 | 5.58015 | 23 |
| 16.26 | 5.44522 | 36.1 |
| 17.79 | 4.98045 | 44.2 |
| 19.04 | 4.65737 | 33.3 |
| 20.05 | 4.42292 | 21.3 |
| 21.87 | 4.05983 | 46.7 |
| 23.47 | 3.78642 | 25.7 |
| 23.83 | 3.73095 | 19 |
| 24.99 | 3.55898 | 90.8 |

In one embodiment a process for preparing highly pure crystalline Form B of rucaparib camsylate includes the steps of:

a) reacting a form of rucaparib free base with DL-10-camphorsulfonic acid or racemic camphorsulfonic acid in a suitable solvent; and b) isolating highly pure crystalline rucaparib camsylate Form B.

Figure 7:
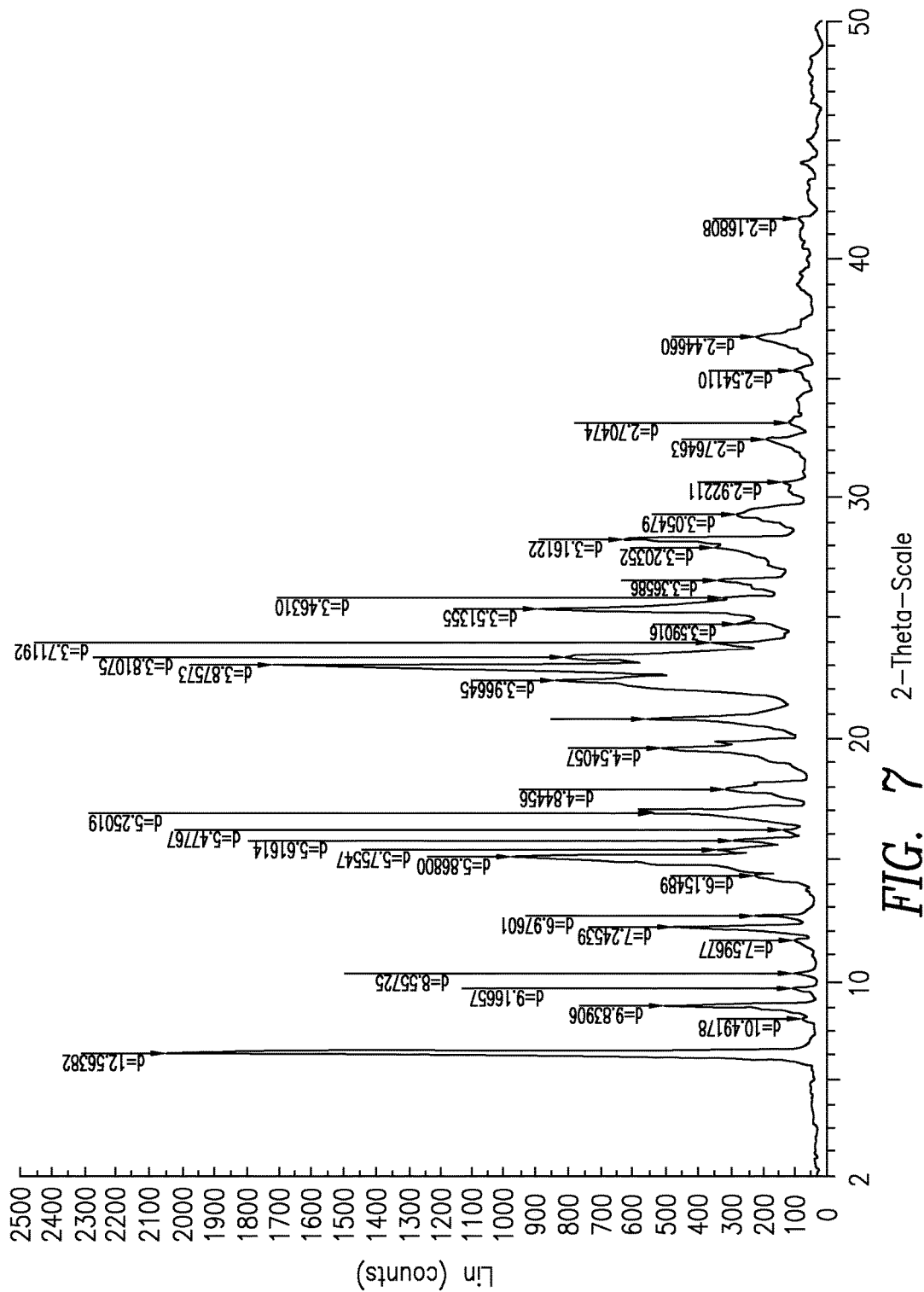
FIG. 7 is a graphical depiction of a characteristic XRPD pattern of rucaparib free base obtained using copper K-alpha$_1$ X-rays at a wavelength of 1.5406 Ångstroms according to an embodiment of the present disclosure.

Any physical form of rucaparib or its camsylate salt may be utilized in step (a) of the process. In one embodiment the form of rucaparib is rucaparib free base (see, e.g., FIG. 7).

In one embodiment the camsylate salt used in step (a) is DL-10-camphorsulfonic acid.

Suitable solvents that may be used in step (a) include but are not limited to alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of step (a) may be less than about 150° C., or less than about 120° C., or less than about 80° C., or less than about 60° C., or any other suitable temperatures. The reaction may be carried out for any desired time period ranging from about 30 minutes to about 10 hours or longer.

The solution obtained in step (a) may be filtered to remove any insoluble particles. Suitable techniques to remove insoluble particles are filtration, micron filter, centrifugation, decantation, and any other techniques known in the art. The solution can be filtered by passing through paper, glass fiber, or other membrane material, or a clarifying agent such as celite. Depending upon the equipment used and the concentration and temperature of the solution, the filtration apparatus may need to be preheated to avoid premature precipitation of solid.

In step b), the highly pure crystalline Form B of rucaparib camsylate may be isolated in a manner known in the art, depending on the solvent used. Suitable isolation techniques include but are not limited to filtration by gravity or by suction/vacuum, distillation, centrifugation, or slow evaporation or the like. In an embodiment, highly pure crystalline Form B of rucaparib camsylate may be isolated by filtration under vacuum and suction drying at a temperature of about 25° C. to about 35° C.

Drying the highly pure crystalline Form B of rucaparib camsylate may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 70° C., at a temperature of about 60° C., at a temperature of about 40° C. or at a temperature of about 30° C. The drying may be carried out for any time periods required for obtaining a desired quality, such as from about 15 minutes to several hours, or longer.

The crystalline form of rucaparib camsylate Form B disclosed herein has advantageous properties selected from at least one of: chemical purity, stability—such as storage stability, stability to dehydration, stability to polymorphic conversion, flowability, solubility, morphology or crystal habit, low hygroscopicity and low content of residual solvents.

In yet further embodiments, a novel crystalline Form gamma of rucaparib camsylate is disclosed having characteristic XRPD peaks at diffraction angles (2θ) 9.5±0.2, 12.73±0.2, 14.77±0.2, 15.16±0.2, 20.62±0.2, 22.33±0.2, 22.63±0.2 and 27.29±0.2.

In still further embodiments, crystalline Form gamma of rucaparib camsylate is disclosed having characteristic XRPD peaks at diffraction angles (2θ) 9.5±0.2, 12.73±0.2, 14.77±0.2, 15.16±0.2, 20.62±0.2, 20.95±0.2, 22.11±0.2, 22.33±0.2, 22.63±0.2, 23.57±0.2 and 27.29±0.2.

In still yet further embodiments, crystalline Form gamma of rucaparib camsylate is disclosed having characteristic XRPD peaks at diffraction angles (2θ) 6.95±0.2, 9.5±0.2, 12.73±0.2, 14.77±0.2, 15.16±0.2, 20.62±0.2, 20.95±0.2, 21.45±0.2, 22.11±0.2, 22.33±0.2, 22.63±0.2, 23.57±0.2, 23.93±0.2, 26.71±0.2, and 27.29±0.2.

Figure 8:
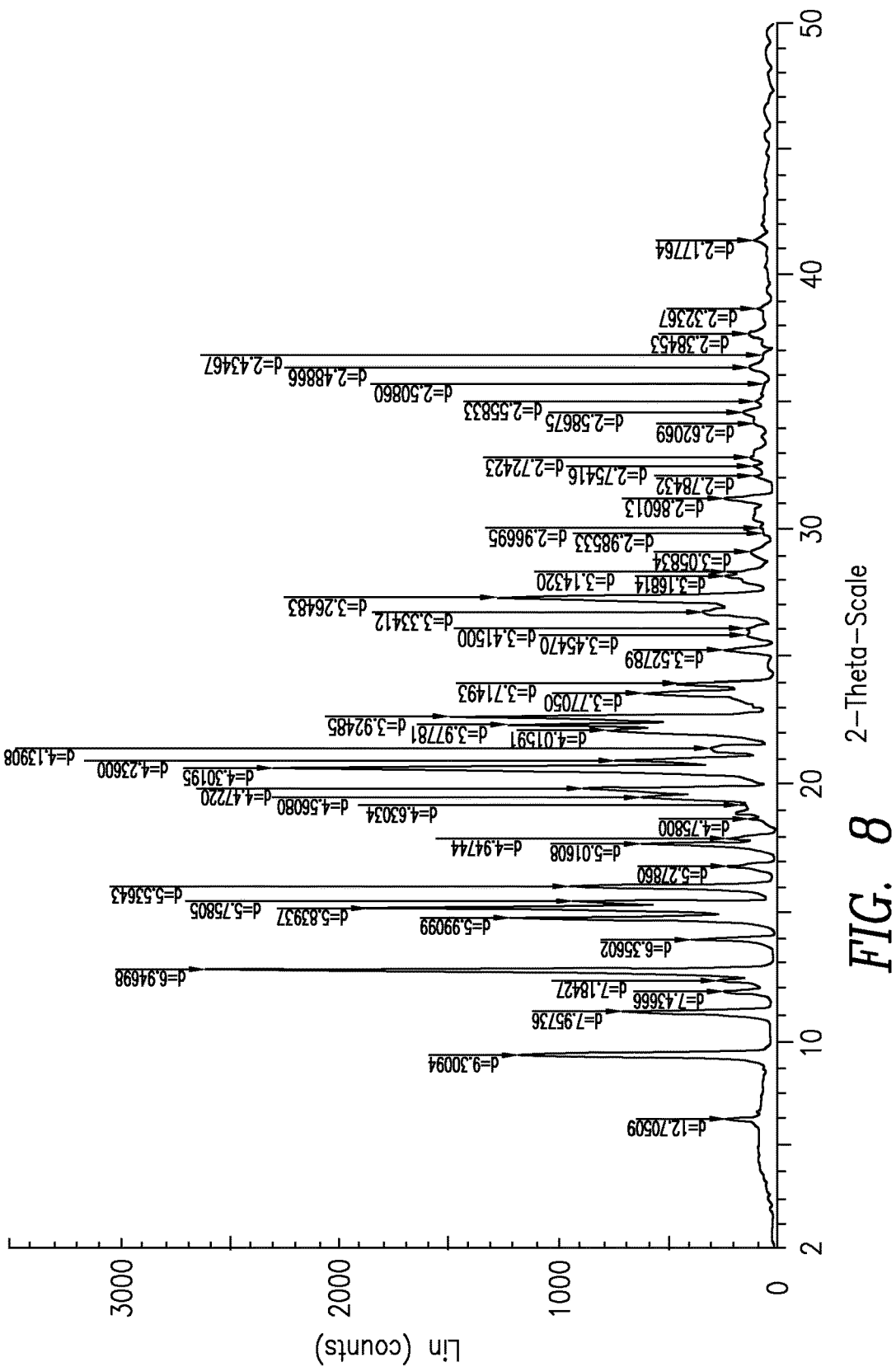
FIG. 8 is a graphical depiction of a characteristic XRPD pattern of rucaparib camsylate Form gamma obtained using copper K-alpha$_1$ X-rays at a wavelength of 1.5406 Ångstroms according to an embodiment of the present disclosure.

In other embodiments, crystalline Form gamma of rucaparib camsylate has an XRPD pattern as illustrated by FIG. 8 and Table 5.

TABLE 5

| Form gamma XRPD of FIG. 8 | | |
| --- | --- | --- |
| Angle (Degree 2θ ± 0.2°) | d value | intensity |
| 6.95 | 1270509 | 8.8 |
| 9.5 | 930094 | 46.1 |
| 12.73 | 694698 | 100 |
| 14.77 | 599099 | 47.4 |
| 15.16 | 583937 | 73 |
| 20.62 | 430195 | 88.8 |
| 20.95 | 423600 | 28.8 |
| 21.45 | 413908 | 12.4 |
| 22.11 | 401591 | 29.6 |
| 22.33 | 397781 | 47.3 |
| 22.63 | 392485 | 57.7 |
| 23.57 | 377050 | 23.4 |
| 23.93 | 371493 | 17.5 |
| 26.71 | 333412 | 13 |
| 27.29 | 326483 | 49.1 |

Figure 9:
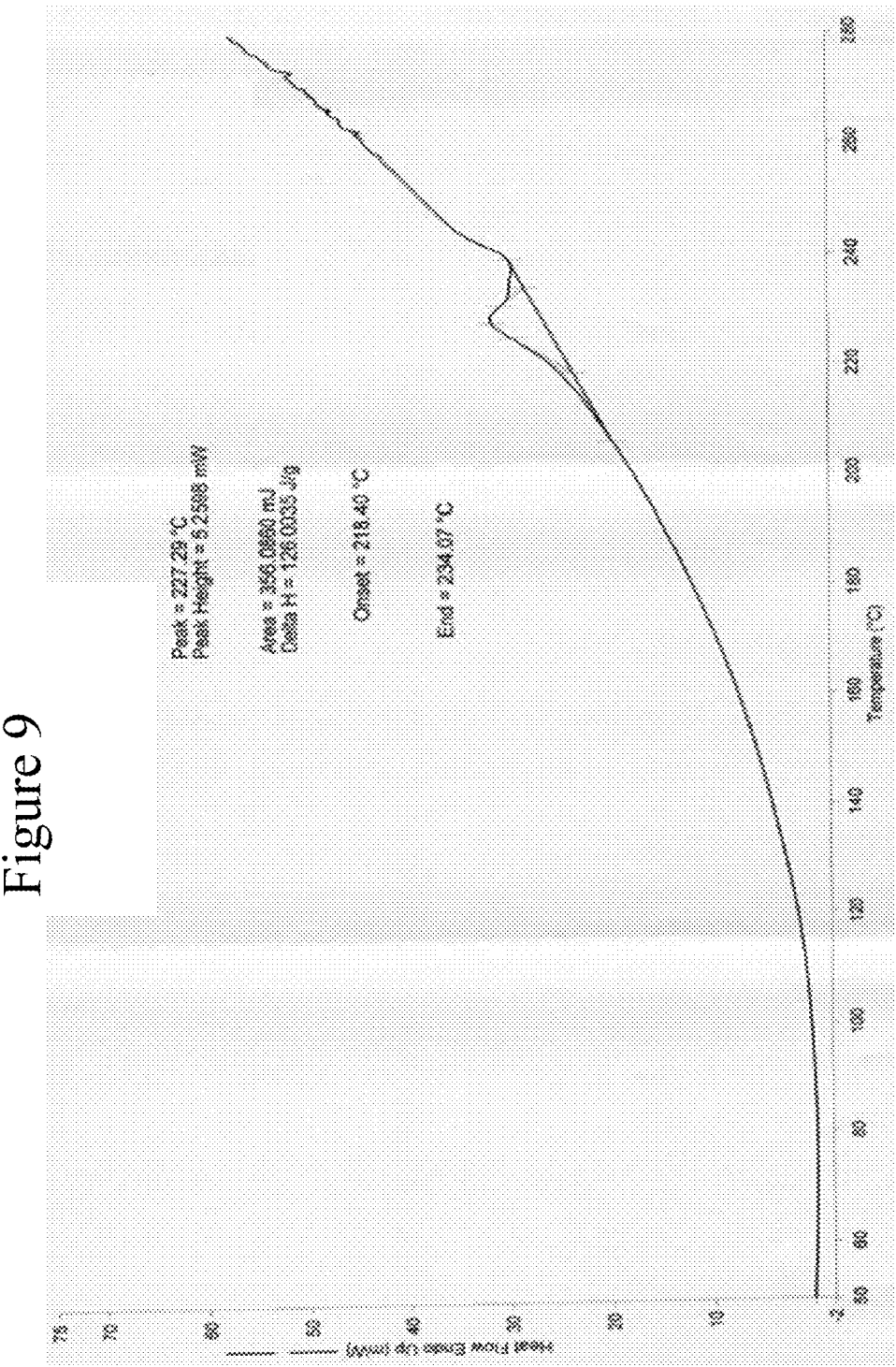
FIG. 9 is a graphical depiction of a characteristic DSC pattern of rucaparib camsylate Form gamma according to an embodiment of the present disclosure.

In still further embodiments the present application provides crystalline Form gamma of rucaparib camsylate having a DSC pattern as illustrated by FIG. 9.

Figure 10:
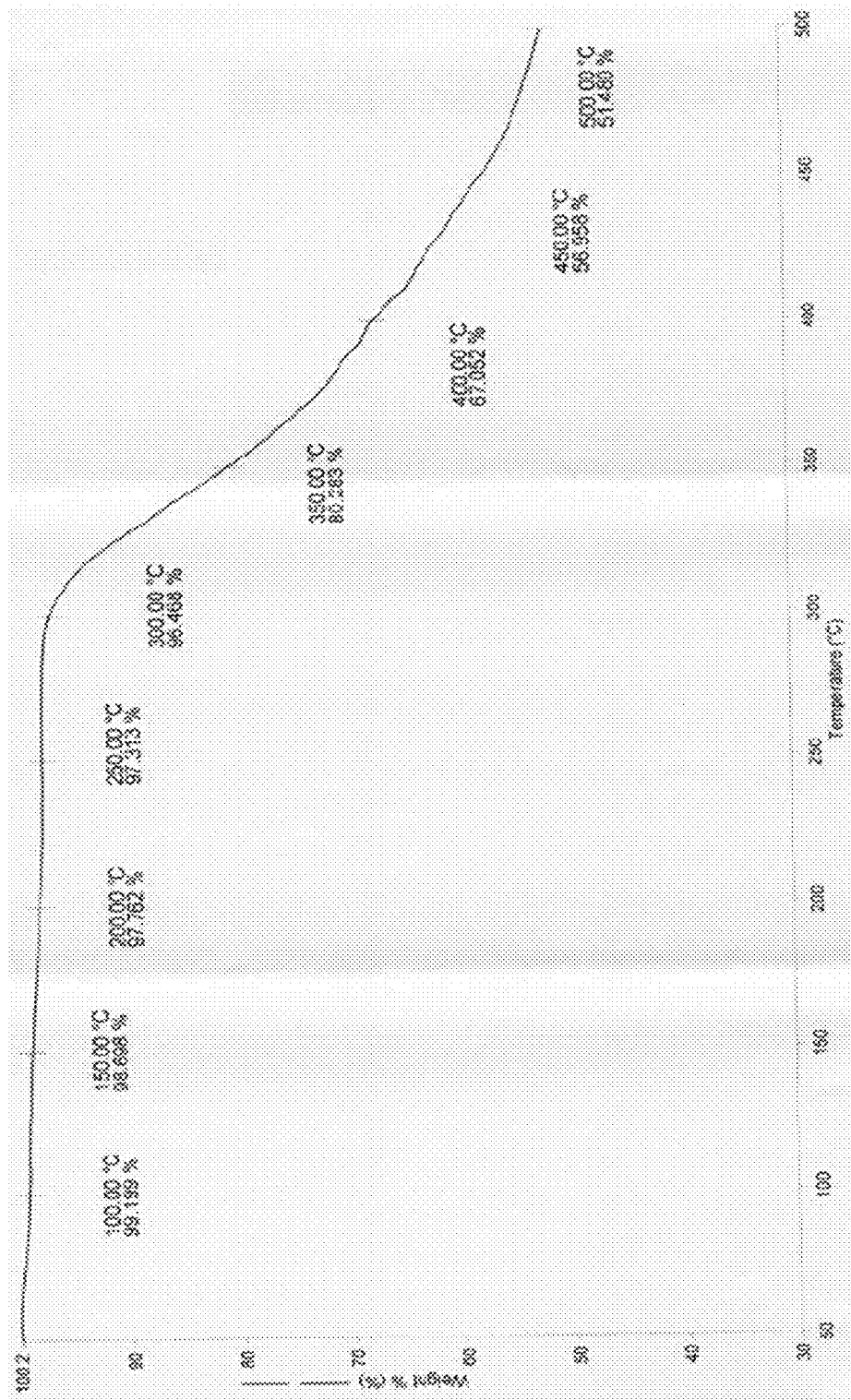
FIG. 10 is a graphical depiction of a characteristic TGA of rucaparib camsylate Form gamma according to an embodiment of the present disclosure.

In still further embodiments the present application provides crystalline Form gamma of rucaparib camsylate having a characteristic thermogravimetric analysis (TGA) as illustrated by FIG. 10.

In another embodiment, the present application provides processes for preparing crystalline Form gamma rucaparib camsylate, including the steps of:

a) combining rucaparib free base with a suitable solvent such as methanol to achieve a clear solution, b) reacting the resulting clear solution with aqueous S-camphorsulfonic acid; and c) isolating crystalline Form gamma rucaparib camsylate from the reaction mixture obtained in step b).

The reaction mixture obtained in step b) may be filtered to remove any insoluble particles. Suitable techniques to remove insoluble particles are filtration, micron filter, centrifugation, decantation, and any other techniques known in the art. The mixture can be filtered by passing through paper, or other membrane material, or a clarifying agent such as celite. Depending upon the equipment used and the concentration and temperature of the solution, the filtration apparatus may need to be preheated to avoid premature precipitation of solid.

Step c) involves isolating Form gamma rucaparib camsylate, which may be induced by using conventional techniques known in the art. For example, useful techniques include but are not limited to, concentrating, cooling, stirring, shaking, combining with an anti-solvent, adding seed crystals, evaporation, flash evaporation, simple evaporation, or the like. The solid that is obtained may carry a small proportion of occluded mother liquor containing a higher percentage of impurities and, if desired, the solid may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, fluidized bed drying. The recovery of crystalline Form gamma can be done by decantation, centrifugation, gravity filtration, suction filtration and like.

Solvent can be removed, optionally under reduced pressures, at temperatures less than about 60° C., less than about 50° C., less than about 40° C. or any other suitable temperatures.

Recovery and optional drying of Form gamma crystalline rucaparib camsylate salt after removal of solvent may be performed in the manner set forth above with respect to Form alpha.

Provided herein are pharmaceutical formulations comprising rucaparib camsylate of Form alpha, Form beta, Form gamma and/or Form B respectively with one or more pharmaceutically acceptable excipients.

The compounds disclosed herein are typically administered in the form of a pharmaceutical composition. Such compositions can be prepared using procedures well known in the pharmaceutical art and include at least one compound disclosed herein. The compounds may also be administered alone or in combination with adjuvants that enhance stability of the compounds, facilitate administration of pharmaceutical compositions containing them in certain embodiments, provide increased dissolution or dispersion, increased inhibitory activity, provide adjunct therapy, and the like. The compounds may be used on their own or in conjunction with other active substances, optionally also in conjunction with other pharmacologically active substances. In general, the compounds may be administered in a therapeutically or pharmaceutically effective amount, but may be administered in lower amounts for diagnostic or other purposes.

When the compounds of the present invention are administered to a human, the compound itself or the compound after admixing with a suitable pharmacologically acceptable carrier, excipient, diluent and the like can be administered orally or parenterally as a safe pharmaceutical composition, such as an oral administration agent (e.g., powder, granule, tablet, capsule etc.), a parenteral administration agent (e.g., injection, an external preparation (e.g., nasal preparation, percutaneous preparation etc.)), a suppository (e.g., rectal suppository, vaginal suppository and the like) and the like.

Thus, administration can be, for example, orally, in the form of solid, semi-solid, lyophilized powder, or liquid dosage forms, such as, for example, tablets, pills, soft elastic and hard gelatin capsules, powders, solutions, suspensions, or the like, preferably in unit dosage forms suitable for simple administration of precise dosages. The pharmaceutical compositions will generally include a conventional pharmaceutical carrier and/or excipient and a compound as disclosed herein as the/an active agent, and, in addition, may include other agents such as but not limited to medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; and H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art. It will be noted that in all of the pharmaceutical compositions enumerated herein, the compounds of the invention are formulated with an acceptable carrier or excipient. The carriers or excipients used must, of course, be acceptable in the sense of being compatible with the other ingredients of the composition and must not be deleterious to the recipient. The carrier or excipient can be a solid or a liquid, or both, and is preferably formulated with the compound of the invention as a unit-dose composition, for example, a tablet. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyvinylpyrrolidone, hydroxypropylcellulose, polyethylene glycol, waxes, and the like. Lubricants include sodium oleate, sodium stearate, magnesium stearate, sodium benzoate, sodium acetate, sodium chloride, and the like. Disintegrants include starch, methyl cellulose, agar, bentonite, xanthan gum, and the like. Examples of a coating agent include hydroxypropylmethylcellulose, ethylcellulose, hydroxymethylcellulose, hydroxypropylcellulose, polyoxyethylene glycol, Tween 80, pluronic F68, cellulose acetate phthalate, hydroxypropylmethyl cellulose phthalate, hydroxymethylcellulose acetate succinate, Eudragit (Rohm Pharm GmbH, Germany, a copolymer of methacrylic acid with acrylic acid), pigment (e.g., titanium oxide, bengara etc.) and the like.

As one of skill in the art would expect, the forms of the compounds of the invention utilized in a particular pharmaceutical formulation will be selected that possess suitable physical characteristics (e.g., water solubility) that is required for the formulation to be efficacious.

For injection, for example, an aqueous injection can be prepared using a compound of the present invention together with a solubilizer (e.g., beta.-cyclodextrins etc.), a dispersing agent (e.g., Tween 80 (Atlas Powder Co., USA), HCO60 (Nikko Chemicals Co., Ltd.), carboxymethylcellulose, sodium alginate etc.), a preservative (e.g., methylparaben, propylparaben, benzyl alcohol, chlorobutanol etc.), an isotonic agent (e.g., sodium chloride, glycerine, sorbitol, glucose etc.) and the like according to a conventional method. Alternatively, an oily injection can be formed by dissolving, suspending or emulsifying as appropriate the compound in a vegetable oil (e.g., olive oil, sesame oil, peanut oil, cottonseed oil, corn oil etc.), propylene glycol and solid like dosage forms for oral administration of the compounds include capsules, tablets, pills, powders, and granules.

For oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

A solid external agent can be produced from the compound of the present invention as it is, or by adding an excipient (e.g., glycol, mannitol, starch, crystalline cellulose etc.), a thickener (e.g., natural gums, cellulose derivative, acrylic polymer etc.) and the like, mixing the same and preparing into a powdery composition. A semi-solid external agent can be produced by a conventional method and preferably used as an aqueous or oily gel, or an ointment. A liquid external preparation can be produced by preparing into an oily or aqueous suspension according to a method employed for production of injection or a similar method. In addition, a pH-adjusting agent (e.g., carbonic acid, phosphoric acid, citric acid, hydrochloric acid, sodium hydroxide etc.), a preservative (e.g., p-oxybenzoic acid esters, chlorobutanol, benzalkonium chloride etc.) and the like may be added as appropriate to a solid, semi-solid or liquid external agent. To be specific, for example, an ointment can be prepared, which contains a compound of the present invention in an amount of about 0.1 to about 100 mg per 1 g, using petrolatum, lanolin and the like as a base material. Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. The formulations may also contain compatible conventional carriers, such as cream or ointment bases and ethanol or oleyl alcohol for lotions. Such carriers may be present as from about 1% up to about 98% of the formulation, preferably they will form up to about 80% of the formulation.

Formulations including a compound of the present invention can be also prepared as an oily or aqueous solid, semi-solid or liquid suppository. The oily base used as appropriate for producing suppository may be, for example, hard fat, higher fatty acid glyceride (e.g., cacao butter, Witepsols (Dynamitnobel Ltd.) etc.), middle fatty acid (e.g., migriol acid (Dynamitnobel Co., Ltd.) etc.), vegetable oil (e.g., sesame oil, soybean oil, cottonseed oil etc.) and the like. As an aqueous base, for example, polyethylene glycols, propylene glycol and the like may be used, and as an aqueous gel base, for example, natural gums, cellulose derivative, vinyl polymer, acrylic polymer and the like may be used as appropriate.

Rucaparib free base used in embodiments disclosed herein may be prepared as depicted in Scheme 1. It will be understood that rucaparib free base made in accordance with any known synthetic scheme may be employed.

Scheme 1

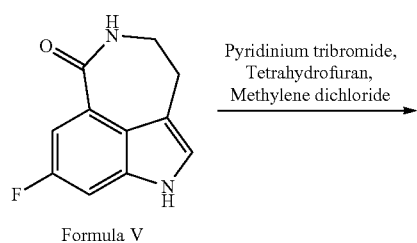

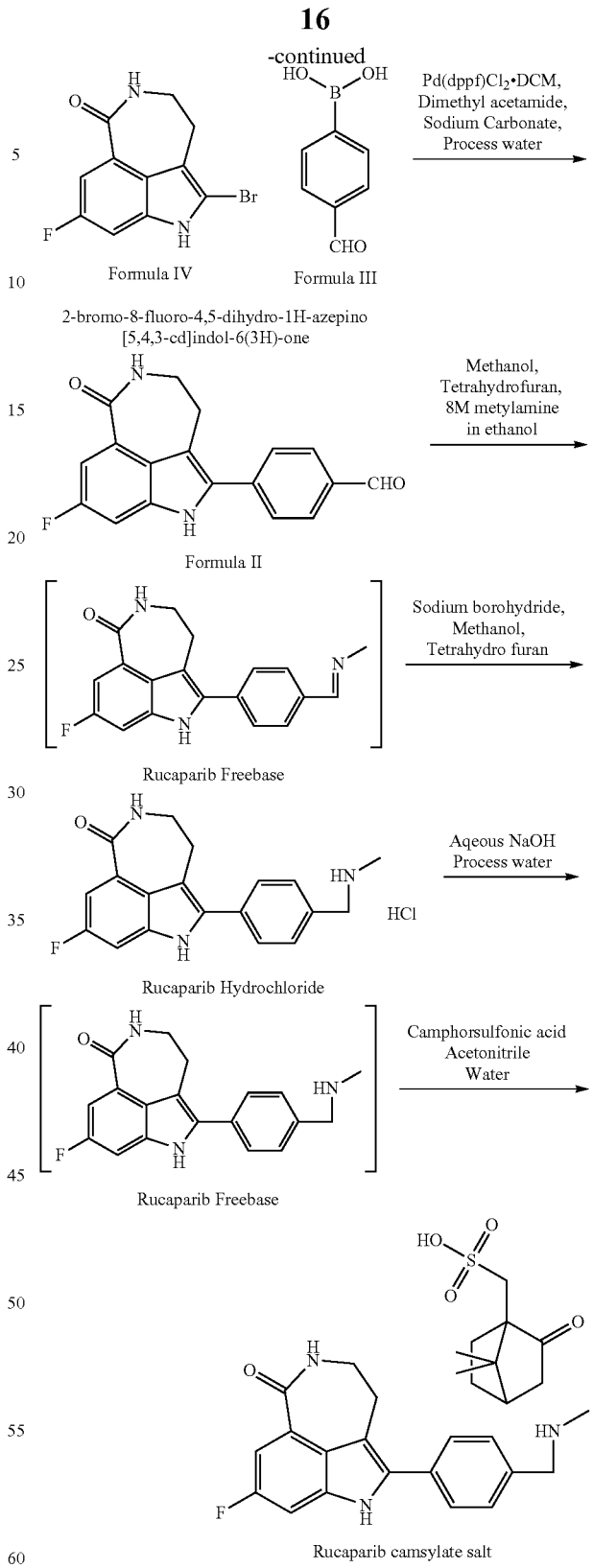

Certain specific aspects and embodiments of the present application will be explained in more detail with reference to the following examples, which are provided only for purposes of illustration and should not be construed as limiting the scope of the present disclosure in any manner.

EXAMPLES

Example 1: Preparation of 2-bromo-8-fluoro-4,5-dihydro-1H-azepino[5,4,3-cd]indol-6(3H)-one (Formula IV)

8-fluoro-4,5-dihydro-1H-azepino[5,4,3-cd]indol-6(3H)-one (Formula V) 100 gm was dissolved in dichloromethane (1000 ml). Pyridinium tribromide (200 gm) was added in the above solution and stirred at 0-5° C. until completion of reaction. Once reaction was complete saturated sodium carbonate solution (500 ml) was added and stirred for 2 hours. The solid was filtered and washed with water (200 ml). The wet cake was taken in acetonitrile (150 ml) and DIPE (150 ml) and stirred at RT for 1 hour. The obtained solid was filtered and washed with acetonitrile (50 ml). The material was dried at 50° C. to get 2-bromo-8-fluoro-4,5-dihydro-1H-azepino[5,4,3-cd]indol-6(3H)-one (Formula IV) (110 gm).

Example 2: Preparation of 4-(8-fluoro-6-oxo-3,4,5,6-tetrahydro-1H-azepino[5,4,3-cd]indol-2-yl)benzaldehyde (formula II)

of 2-bromo-8-fluoro-4,5-dihydro-1H-azepino[5,4,3-cd]indol-6(3H)-one (Formula IV) 100 gm was dissolved in isopropyl alcohol (1600 ml) under nitrogen gas at RT. Added Pd(dppf)Cl$_2$.DCM (7.27 gm) in the above solution and stirred for 1 hour at RT and then heated to 80-85° C. Simultaneously a solution of 4-formyl phenyl boronic acid (Formula III) (63 gm) in isopropyl alcohol (400 ml) at RT was prepared. The solution was cooled to 0-5° C. and sodium carbonate solution (75.5 gm in 1200 ml water) was added slowly. This reaction mass was charged into the above reaction mass and stirred for 3 hours at 80-85° C. Once the reaction was complete the reaction mass was cooled to RT and water added (4000 ml). Once the solid fell out, the reaction mass was stirred for 1 hour at RT. The reaction mass was filtered and washed with water (1000 ml). The wet cake was dissolved in dimethyl acetamide (400 ml) and the solution heated to 80-85° C. and stirred for 30 minutes at 80-85° C., and then cooled to 60-65° C. Methanol (400 ml) was charged to the solution at 60-65° C. and stirring proceeded for 30 mins. Water was charged (2000 ml) at RT and stirring proceeded for 30 mins. The reaction mass was filtered and washed with methanol (100 ml). The solid was dried at 55-60° C. to afford 4-(8-fluoro-6-oxo-3,4,5,6-tetrahydro-1H-azepino[5,4,3-cd]indol-2-yl)benzaldehyde (Formula II) (90 gm).

Example 3: Preparation of Rucaparib Hydrochloride 4-(8-fluoro-6-oxo-3,4,5,6-tetrahydro-1H-azepino[5,4,3-cd]indol-2-yl)benzaldehyde (Formula II) was dissolved in a solution mixture of methanol (1000 ml) and THF (500 ml) at RT. 8.0 molar mono methyl amine in methanol (1000 ml) was added in the above solution at 0-5° C. and then the solution was stirred for 2 hours at RT. After completion of reaction, solvent was distilled (approx. 300 ml) and then stirring proceeded for 2 hours at RT. The solid was filtered and washed with methanol (200 ml). The wet cake was dissolved in methanol (1500 ml) and THF (500 ml) and then NaBH$_4$ (60 gm) was added at 0-5° C. The reaction mass was stirred for 2 hours at RT. Methanol (500 ml), water (400 ml) and conc. hydrochloric acid (400 ml) were charged and further stirring proceeded for 2 hours. The reaction mass was filtered and washed with methanol (200 ml). The solid was dried at 38-42° C. to obtain rucaparib hydrochloride.

Example 4: Preparation of Rucaparib Free Base

Rucaparib hydrochloride was added in solution containing 40% sodium hydroxide solution (100 ml) in water (500 mL), methanol and 300 mL process water at 0-5° C. The reaction mass was stirred for 12 hours at 0-5° C. After completion of salt formation, the solid was filtered, washed with water (200 ml). The material was dried at 50-55° C. to afford rucaparib camsylate free base (Formula III).

Example 5: Preparation of Rucaparib Camsylate Form Alpha

Rucaparib base (0.2 g) and S-camphorsulfonic acid (0.14 g) were dissolved in a 1,4-dioxane-water (1:1; 6 mL) mixture at 30° C. The clear solution was stirred at 30° C. for 12 h. The resulting product was filtered and dried at 50° C. under vacuum for 2 h. The resulting product was identified as crystalline (S)-rucaparib camsylate salt Form alpha.

Example 6: Preparation of Rucaparib Camsylate Form Alpha

Rucaparib base (2 g) and S-camphorsulfonic acid (1.5 g) were dissolved in 1,4-dioxane-water (1:1; 20 mL) mixture at 30° C. The clear solution was stirred at 30° C. for 1 h. The clear solution was seeded with Form alpha (20 mg). The resulting product was filtered and dried at 50° C. under vacuum for 2 h. The resulting product was identified as crystalline (S)-rucaparib camsylate salt Form alpha.

Example 7: Preparation of Rucaparib Camsylate Form Beta

Rucaparib base (0.1 g) and DL-10-camphorsulfonic acid (0.072 g) were dissolved in a 1,2-dimethoxy ethane and water mixture (1:1; 3 mL) at 30° C. The clear reaction mass was filtered to remove the undissolved particulates and stirred at 30° C. for 5 h. The resulting product was filtered, washed with isopropyl ether (1 mL) and dried at 40° C. under vacuum for 3 h. The resulting product was identified as crystalline rucaparib camsylate salt Form beta.

Example 8: Preparation of Rucaparib Camsylate Form Beta

Rucaparib base (0.1 g) and DL-10-camphorsulfonic acid (0.072 g) were dissolved in acetonitrile and water mixture (1:1; 4 mL) at 55° C. The clear reaction mass was filtered to remove the undissolved particulates and stirred at 30° C. for 12 h. The resulting product was filtered, washed with isopropyl ether (1 mL) and dried at 80° C. under vacuum for 3 h. The resulting product was identified as crystalline rucaparib camsylate salt Form beta.

Example 9: Preparation of Rucaparib Camsylate Form Beta

Rucaparib base (0.1 g) and DL-10-camphorsulfonic acid (0.072 g) were dissolved in a 2-methoxyethanol and water mixture (1:1; 4 mL) at 55° C. The clear reaction mass was filtered to remove the undissolved particulates and stirred at 30° C. for 12 h. The resulting product was filtered, washed with isopropyl ether (1 mL) and dried at 80° C. under vacuum for 3 h. The resulting product was identified as crystalline rucaparib camsylate salt Form beta.

Example 10: Preparation of Rucaparib Camsylate Form Beta

Rucaparib base (0.1 g) and DL-10-camphorsulfonic acid (0.072 g) was dissolved in N-methyl morpholine and water mixture (1:2; 3 mL) at 55° C. The clear reaction mass was filtered to remove the undissolved particulate and stirred at 30° C. for 12 h. The resulting product was filtered, washed with iso-propyl ether (1 mL) and dried at 80° C. under vacuum for 3 h. The resulting product was identified as crystalline rucaparib camsylate salt Form beta.

Example 11: Preparation of Rucaparib Camsylate Form B

Rucaparib base (0.1 g) and DL-10-camphorsulfonic acid was dissolved in methanol (2.5 mL) at 30° C. The clear reaction mass was filtered to remove the undissolved particulates. Isopropyl ether was added and stirring at 25-30° C. proceeded for 30 min. The resulting product was identified as crystalline rucaparib camsylate salt Form B.

Example 12: Preparation of Rucaparib Camsylate Form B

Rucaparib base (2 g) and DL-10-camphorsulfonic acid was dissolved in THF-water (20:2 mL) mixture at 30° C. The clear solution was stirred at 30° C. for 5 h. The resulting product was filtered and dried at 50° C. under vacuum for 2 h. The resulting product was identified as crystalline rucaparib camsylate salt Form B.

Example 13: Preparation of Rucaparib Camsylate Form Gamma

Rucaparib (5 g) was slurried in 25 mL of methanol S-camphorsulfonic acid (3.6 g) was dissolved in 25 mL of water and added dropwise to the methanolic solution. The reaction mixture was heated at 70-80° C. to obtain a clear solution. The clear reaction mass was filtered to remove undissolved particulates, cooled and stirred at 30° C. for 3 h. The resulting product was filtered, washed with water (20 mL) and dried at 60° C. under vacuum for 12 h. The resulting product was identified as novel crystalline rucaparib camsylate salt Form gamma. Form gamma included characteristic 2-theta values as contained in FIG. 8, DSC peak at 227.29° C. (FIG. 9), and thermogravimetric analysis as shown in FIG. 10.

Although the compounds, schemes and methods of the present disclosure have been described with reference to exemplary embodiments thereof, the present disclosure is not limited thereby. Indeed, the exemplary embodiments are implementations of the disclosed methods are provided for illustrative and non-limitative purposes. Changes, modifications, enhancements and/or refinements to the disclosed methods may be made without departing from the spirit or scope of the present disclosure. Accordingly, such changes, modifications, enhancements and/or refinements are encompassed within the scope of the present invention. All publications, patent applications, patents, figures and other references mentioned herein are expressly incorporated by reference in their entirety.

What is claimed is:

1. A crystalline Form beta of rucaparib camsylate having an XRPD pattern comprising peaks at diffraction angles (2θ) of 9.58±0.2, 12.75±0.2, 14.56±0.2, 15.05±0.2, 20.76±0.2 and 22.45±0.2.

2. The crystalline Form beta of rucaparib camsylate of claim 1 comprising XRPD peaks at diffraction angles (2θ) of 6.86±0.2, 9.58±0.2, 12.75±0.2, 14.56±0.2, 15.05±0.2, 15.41±0.2, 15.99±0.2, 20.76±0.2, 22.45±0.2 and 27.44±0.2.

3. The crystalline Form beta of rucaparib camsylate of claim 1 comprising XRPD peaks at diffraction angles (2θ) of 6.86±0.2, 9.58±0.2, 11.08±0.2, 12.75±0.2, 14.56±0.2, 15.05±0.2, 15.41±0.2, 15.99±0.2, 19.35±0.2, 19.59±0.2, 20.76±0.2, 22.11±0.2, 22.45±0.2, 23.80±0.2, and 27.44±0.2.

4. The crystalline Form beta of rucaparib camsylate of claim 1 characterized by an XRPD pattern substantially as shown in FIG. 3.

5. The crystalline form Beta of rucaparib camsylate of claim 1 characterized by a DSC pattern substantially as shown in FIG. 4.

6. A method of preparing the crystalline Form beta of rucaparib camsylate of claim 1 comprising the steps of a) reacting rucaparib free base with DL-10-camphorsulfonic acid in a solvent; and b) isolating the crystalline Form beta of rucaparib camsylate.

7. A pharmaceutical composition comprising the crystalline Form beta of rucaparib camsylate of claim 1 and one or more pharmaceutically acceptable excipients.

8. A crystalline Form gamma of rucaparib camsylate having an XRPD pattern comprising peaks at diffraction angles (2θ) of 9.5±0.2, 12.73±0.2, 14.77±0.2, 15.16±0.2, 20.62±0.2, 22.33±0.2, 22.63±0.2 and 27.29±0.2.

9. The crystalline Form gamma of rucaparib camsylate of claim 8 comprising XRPD peaks at diffraction angles (2θ) of 9.5±0.2, 12.73±0.2, 14.77±0.2, 15.16±0.2, 20.62±0.2, 20.95±0.2, 22.11±0.2, 22.33±0.2, 22.63±0.2, 23.57±0.2 and 27.29±0.2.

10. The crystalline Form gamma of rucaparib camsylate of claim 8 comprising XRPD peaks at diffraction angles (2θ) of 6.95±0.2, 9.5±0.2, 12.73±0.2, 14.77±0.2, 15.16±0.2, 20.62±0.2, 20.95±0.2, 21.45±0.2, 22.11±0.2, 22.33±0.2, 22.63±0.2, 23.57±0.2, 23.93±0.2, 26.71±0.2, and 27.29±0.2.

11. The crystalline Form gamma of rucaparib camsylate of claim 8 characterized by an XRPD pattern substantially as shown in FIG. 8.

12. The crystalline Form gamma of rucaparib camsylate of claim 8 characterized by a DSC pattern substantially as shown in FIG. 9.

13. The crystalline Form gamma of rucaparib camsylate of claim 8 characterized by a thermogravimetric analysis (TGA) as illustrated by FIG. 10.

14. A method of preparing the crystalline Form gamma of rucaparib camsylate of claim 8 comprising the steps of a) combining rucaparib free base with a solvent to achieve a clear solution, b) reacting the clear solution with aq. S-camphorsulfonic acid; and c) isolating the crystalline form gamma rucaparib camsylate.

15. The method of claim 14 wherein the solvent is methanol.

16. A pharmaceutical composition comprising the crystalline Form gamma of rucaparib camsylate of claim 8 and one or more pharmaceutically acceptable excipients.

* * * * *